United States Patent
Wo et al.

(10) Patent No.: US 8,535,541 B2
(45) Date of Patent: Sep. 17, 2013

(54) METHOD FOR SEPARATING IMMUNOMAGNETIC BEAD LABELED PARTICULATES

(75) Inventors: Andrew Man Chung Wo, Taipei (TW); Yu-Cheng Pan, Taipei (TW); Ken-Chao Chen, Taipei (TW); Chen-Lin Chen, Taipei (TW)

(73) Assignee: National Taiwan University, Taipei (TW)

( * ) Notice: Subject to any disclaimer, the term of this patent is extended or adjusted under 35 U.S.C. 154(b) by 432 days.

(21) Appl. No.: 12/861,989

(22) Filed: Aug. 24, 2010

(65) Prior Publication Data

US 2011/0059500 A1    Mar. 10, 2011

(30) Foreign Application Priority Data

Sep. 10, 2009  (TW) ............................... 98130484 A (51) Int. Cl.
  *B01D 21/26*  (2006.01)
  *B01D 35/06*  (2006.01)
  *G01N 33/543*  (2006.01)

(52) U.S. Cl.
  USPC ............... 210/695; 494/37; 436/45; 436/177; 436/526; 435/173.9; 435/287.2; 435/287.3; 422/72; 422/415; 422/506; 210/787; 210/806

(58) Field of Classification Search
  USPC .......... 494/37; 436/45, 177, 526; 435/173.9, 435/287.2, 287.3; 422/72, 415, 506; 210/695, 210/787, 806
  See application file for complete search history.

(56) References Cited

U.S. PATENT DOCUMENTS

| 5,565,105 | A | 10/1996 | Thakor |
| 6,723,510 | B2 | 4/2004 | Lubenow et al. |
| 8,226,826 | B2 * | 7/2012 | Wo et al. .................... 435/173.9 |
| 2005/0221281 | A1 | 10/2005 | Ho |
| 2008/0035579 | A1 * | 2/2008 | Lee et al. ....................... 210/695 |

* cited by examiner

Primary Examiner — David A Reifsnyder
(74) Attorney, Agent, or Firm — Rosenberg, Klein & Lee (57) ABSTRACT

Disclosed is a method for separating immunomagnetic bead labeled particulates. A carrier board is formed with at least one flow channel structure, which includes an inner reservoir, an outer reservoir, and at least one micro flow channel in communication with the inner reservoir and the outer reservoir. The method includes labeling target particulates with immunomagnetic bead, introducing a sample fluid into the inner reservoir, and applying a magnetic force and a driving force, wherein the driving force drives the particulates not labeled with immunomagnetic bead to flow through the micro flow channel to the outer reservoir, while the magnetic force attracts the particulates labeled with the immunomagnetic bead to retain in the inner reservoir. The driving force may be centrifugal force, pressure, or surface tension.

10 Claims, 11 Drawing Sheets

FIG.14

METHOD FOR SEPARATING IMMUNOMAGNETIC BEAD LABELED PARTICULATES

FIELD OF THE INVENTION

The present invention relates to separation of cells, and in particular to a method for separating immunomagnetic bead labeled particulates.

BACKGROUND OF THE INVENTION

Detection and quantification of cancer cells or rare cells present in body fluids are regarded as a potential indicator for clinical diagnoses, prognostication, and biomedicine research. For example, circulating tumor cells (CTC) are rare in the blood of patients with metastatic cancer, and it is possible to monitor the response of CTC to adjuvant therapy. To detect and quantify these rare cells present in body fluids, these rare cells must be separated first. Thus, techniques of particulates separation have been developed.

Various techniques of particulates separation are now available for separation of cells, including fluorescence activated cell separation (FACS), dielectrophoresis (DEP) cell separation, separation techniques that employ massively parallel microfabricated sieving devices, magnetically activated cell separation (MACS), and other techniques that uses optics and acoustics. Among these cell separation techniques, FACS and MACS are most often used.

Although it is often used, FACS suffers several drawbacks, including high cost, difficulty in disinfection, consuming a great amount of sample in the operation thereof. Contrary to FACS, MACS is efficient to obtain a major quantity of target cells in a short period and reduces the consumption of sample. However, these cells must be transferred to a slide or an observation platform before they can be observed with a microscope. Such a process of transfer often leads to a great loss of cells.

U.S. Pat. No. 5,565,105 discloses a magnetocentrifugation method, wherein charged particles are deposited in a rotor board and a magnetic field is vertically applied to the rotor board. When the rotor board is brought into rotation, the charged particles carried by the rotor board are caused to move through the magnetic field, whereby the charged particles are subjected to Lorentz force and separate from non-charged particles.

U.S. Pat. No. 6,723,510 discloses a method for separating particles with minimized particle loss, wherein a detergent containing matrix beads is bound with a sample containing target particles in order to reduce the loss of the target particles in the separation processes.

SUMMARY OF THE INVENT

The conventional separation techniques suffer limited effectiveness of separation and extended time cycle of separation operation, and is also disadvantageous in that the sensitivity of detection and separation is constrained, the result of separation is poor, and direct observation cannot be made immediately after separation, which leads to great losses of cells caused by transferring the separated cells to a slide or an observation platform.

Thus, an objective of the present invention is to provide a method for separating immunomagnetic bead labeled particulates, which allows labeled particulates to be separated from a fluid sample.

The solution adopted in the present invention to overcome the problems of the conventional techniques comprises a carrier board that forms at least one flow channel structure. Each flow channel structure comprises an inner reservoir, an outer reservoir, and at least one micro flow channel communicating between the inner and outer reservoirs. Target particulates contained in the sample fluid are first labeled with immunomagnetic beads, and then the sample fluid is injected into the inner reservoir. A magnetic attraction force is applied and a driving force is further applied according to a predetermined driving strength modulation mode to drive the sample fluid to flow so that the non-target particulates that are not labeled with the immunomagnetic beads are driven to entrain the sample fluid passing through the micro flow channel and are thus separated and collected in the outer reservoir. On the other hand, the target particulates that are labeled with the immunomagnetic beads are retained in the inner reservoir by being attracted by the magnetic attraction force.

In a preferred embodiment according to the present invention, the magnetic attraction force covers both the inner reservoir and the micro flow channel so that the target particulates that are labeled with the immunomagnetic beads can be retained in both the inner reservoir and the micro flow channel. The driving strength modulation mode comprises first applying a driving force of a first driving strength to drive the sample fluid to flow, and then applying at least a driving force that has a second driving strength exceeding the first driving strength to drive the sample fluid to flow. Alternatively, a driving force of a first driving strength is applied to cause the sample fluid to flow so that a primary separation is made between the non-target particulates that are not labeled with the immunomagnetic beads and the target particulates that are labeled with the immunomagnetic beads contained in the sample fluid; and then a driving force of a second driving strength is applied to cause the sample fluid to flow so as to drive the non-target particulates that are not labeled with the immunomagnetic beads to entrain the sample fluid passing through the micro flow channel and thus separated and collected in the outer reservoir. The driving force may be a centrifugal force, a pressure, or a surface tension.

After the target particulates and the non-target particulates are separated, a further step of observing the target particulates that are labeled with the immunomagnetic beads is performed and a step of cutting a portion of the carrier board and the target particulates that are labeled with the immunomagnetic beads off the carrier board is also performed.

The technical solution of the present invention shows some advantages over the existing technology. Fore example, adoption of the technical solution according to the present invention allows for easy separation of target particulates from a sample fluid that contains the target particulates and non-target particulates. The method can be performed with a platform constructed in accordance with the present invention, which is easy to manufacture, uses materials that are easily accessed, and thus shows an advantage of low manufacturing cost.

Further, the separation method according to the present invention does not need to worry about the complication of a sample fluid, where target particulates contained in the sample fluid can be labeled with specific immunomagnetic beads no matter how many types of particulates are contained in the sample fluid. After the separation, all the non-target particulates will be separated and collected in the outer reservoir to allow easy access and collection of the target particulates. Thus the performance of the method is intuitive and provides improved result of separation. The present invention is not only applicable to the separation of limited types of particulates, but is also suitable for separating target particulates from a complicated sample fluid that contains a large number of types of particulates in a practical application.

Further, the present invention also provides a driving strength modulation process that when combined with the separation method of the present invention provides even improved result of separation. In addition, observation can be directly made on the target particulates that are combined on the carrier board without any transferring of the particulates to a slide or an observation platform, so that the loss of cells can be kept low. If desired, subsequent processing can be carried out by performing a cutting operation on the carrier board so that the target particulates can be recovered efficiently and effectively to allow for subsequent cultivation of cells and experimentation.

BRIEF DESCRIPTION OF THE DRAWINGS

The present invention will be apparent to those skilled in the art by reading the following description of the best modes for carrying out the present invention, with reference to the attached drawings, in which.

DETAILED DESCRIPTION OF THE PREFERRED EMBODIMENTS

Figure 1:
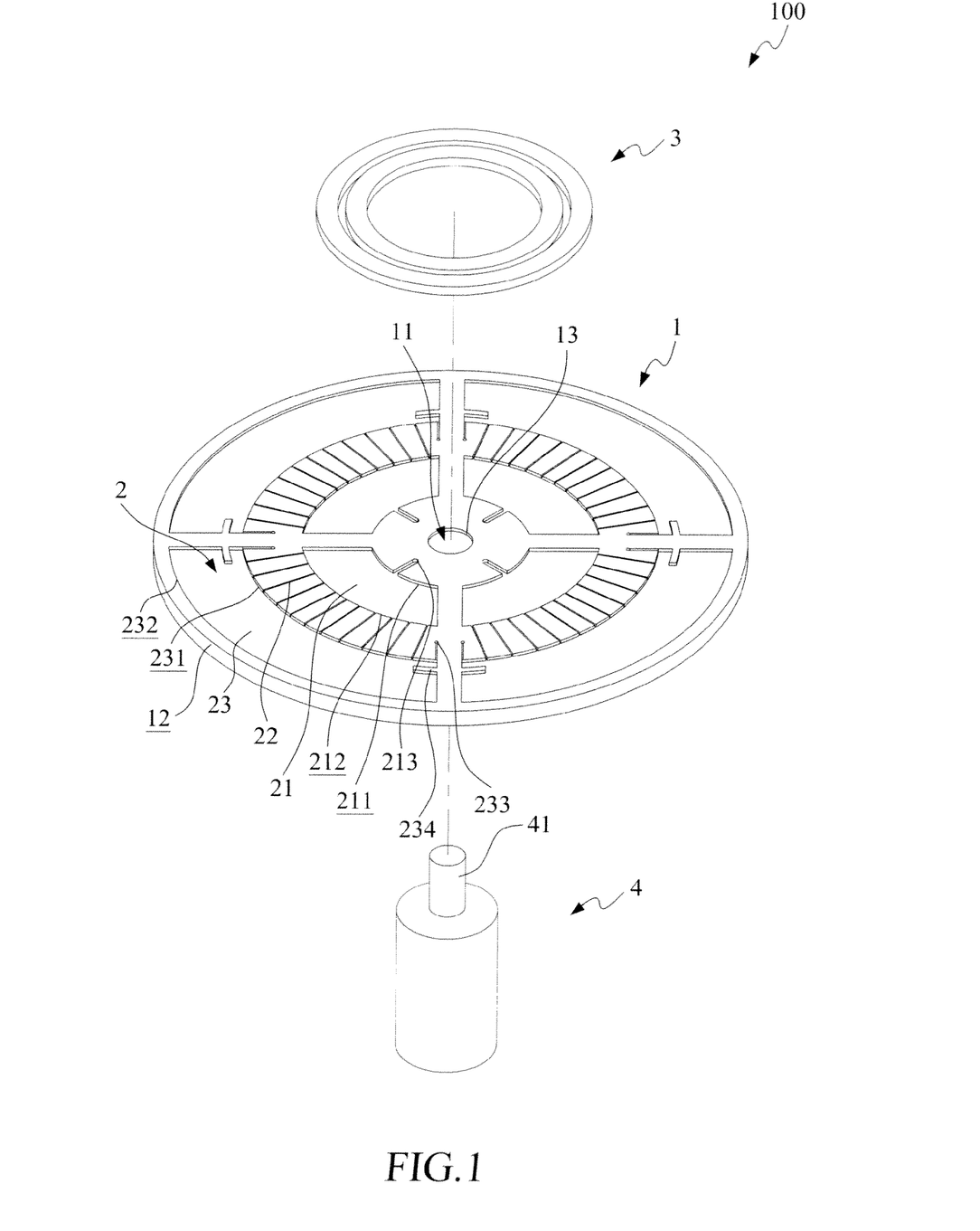
FIG. 1 is a perspective view showing a separation platform with which particulate separation according to the present invention is performed.

With reference to the drawings and in particular to FIG. 1, which shows a separation platform 100 with which a method for separating particulates according to the present invention is performed, the separation platform 100 comprises a carrier board 1 in which at least one flow channel structure 2 is formed. Arranged above the carrier board 1 is a magnetic attraction unit 3, while below the carrier board 1, a driving device 4 that causes the carrier board 1 to spin.

Figure 2:
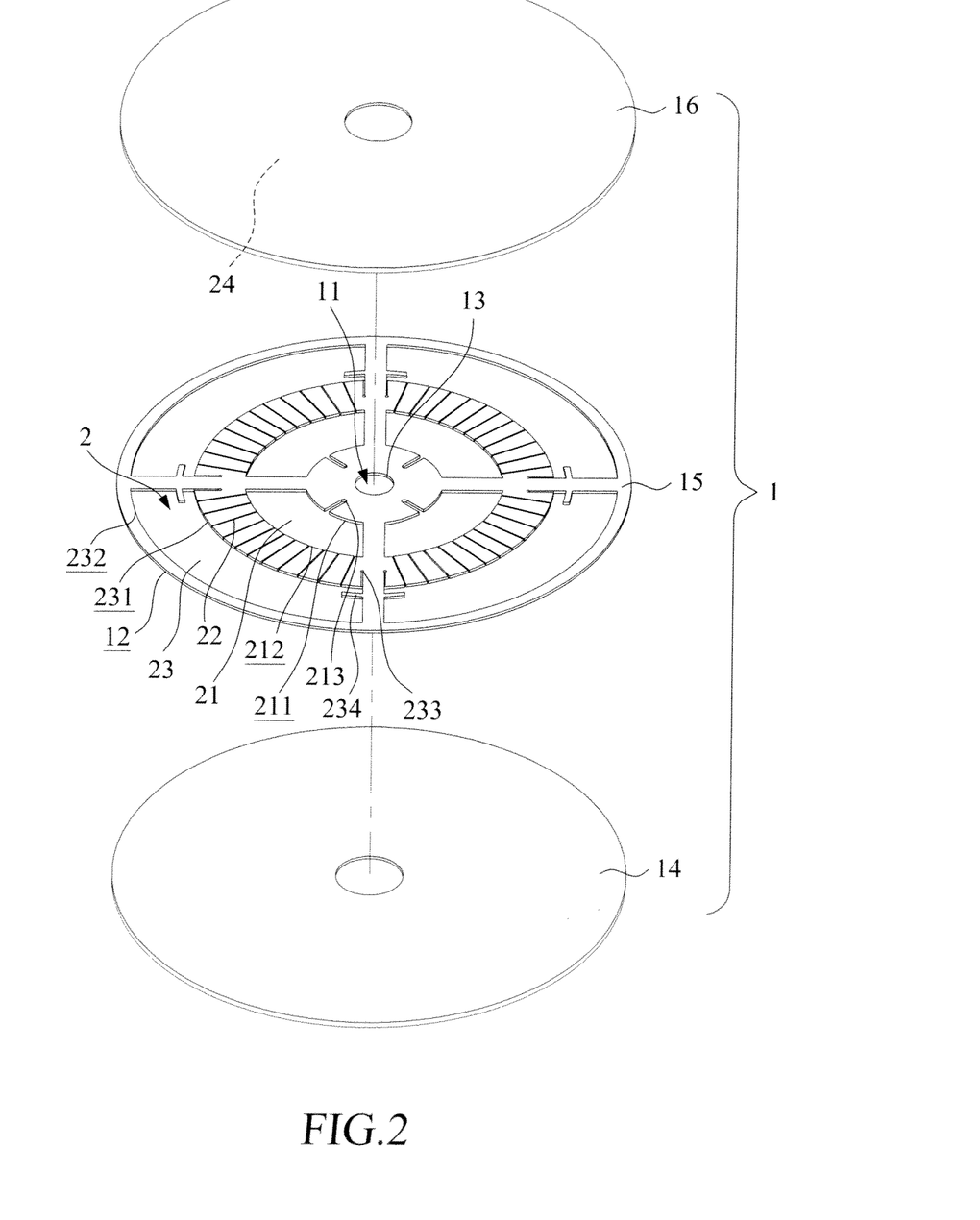
FIG. 2 is an exploded view of a carrier board in accordance with the present invention.

Also referring to FIG. 2, which shows an exploded view of the carrier board according to the present invention, the carrier board 1 has a geometric center 11 and an outer circumferential rim 12. A central hole 13 is defined at the geometric center 11 and the central hole 13 receives and is coupled to a spindle 41 of the driving device 4. In the instant embodiment, the carrier board 1 has a three-layer configuration, which includes, in sequence from the bottom side to the top side, a bottom base layer 14, a middle, flow channel structure layer 15, and a top cover layer 16.

The flow channel structure 2 is formed in the flow channel structure layer 15. The base layer 14 and the flow channel structure layer 15 are made of acrylic resins, such as polymethylmethacrylate (PMMA), and the cover layer 16 is comprised of a thin transparent film. In the manufacturing, the flow channel structure layer 15 is processed by CO2 laser machining to form the flow channel structure 2. The flow channel structure layer 15 is then bonded to the base layer 14 and the cover layer 16 is applied atop the flow channel structure layer 15 to completely cover and enclose the flow channel structure 2. This way is advantageous by being easy to manufacture, using low cost materials, and reducing manufacturing costs.

Apparently, the flow channel structure layer 15 can alternatively be of a multiple-layered structure formed by stacking multiple layers of boards together. The carrier board 1 can be alternatively made a single-layered structure formed of various materials suitable for processing and machining, not limited to acrylic reins. The flow channel structure 2 can alternatively be formed by employing other types of laser machining, or CNC machining, micromachining, and injection molding.

Figure 3:
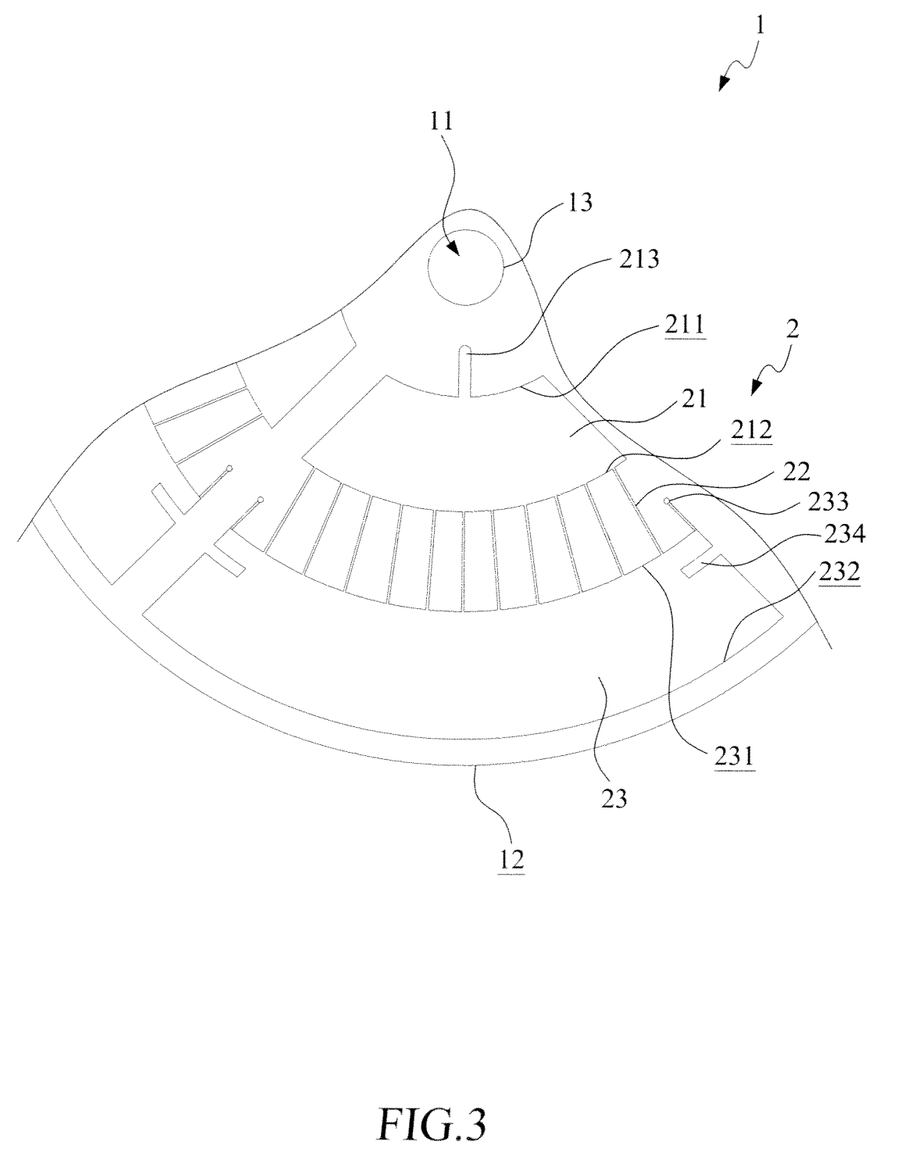
FIG. 3 is a top plan view of a portion of the carrier board in accordance with the present invention.

Also referring to FIG. 3, which shows a top plan view of a portion of the carrier board, the carrier board 1 forms four flow channel structures 2. Each of the flow channel structures 2 comprises an inner reservoir 21, a plurality of micro flow channels 22, and an outer reservoir 23, which are sequentially arranged in a direction from the geometric center 11 of the carrier board 1 toward the outer circumferential rim 12.

The inner reservoir 21 has an inner bank 211 and an outer bank 212. The inner bank 211 is adjacent to the geometric center 11 of the carrier board 1. The outer bank 212 is in fluid communication with the plurality of micro flow channels 22. The inner bank 211 of the inner reservoir 21 forms a fluid inlet opening 213 that extends in a direction toward the geometric center 11 of the carrier board 1.

The outer reservoir 23 has an inner bank 231 and an outer bank 232. The inner bank 231 is in fluid communication with the plurality of micro flow channels 22. The outer bank 232 is adjacent to the outer circumferential rim 12 of the carrier board 1.

Figure 4:
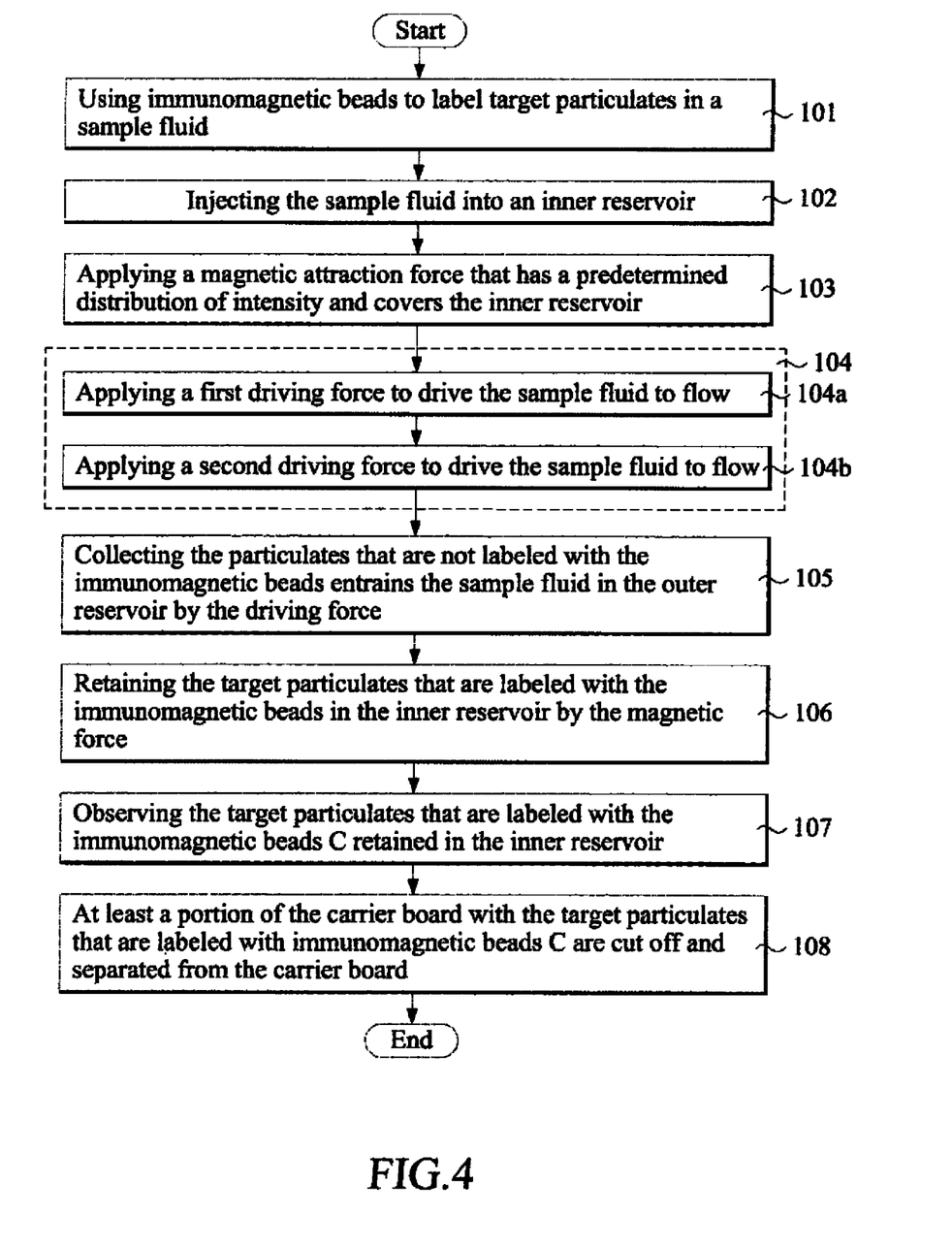
FIG. 4 is a flow chart illustrating a process in accordance with a first embodiment of the present invention.

Referring to FIG. 4, which shows a flow chart of a process in accordance with a first embodiment of the present invention, and reference being also made to FIGS. 1-3 and 5-9, the process of the first embodiment of the present invention will be explained as follows.

Firstly, a sample fluid 5 that contains target particulates M and non-target particulates J is provided and immunomagnetic beads C having a predetermined bonding molecule P is used to label the target particulates M (Step 101). In the instant embodiment, the sample fluid 5 contains two types of particulate, of which the non-target particulates J are Jurkat cells, which are human lymphoma cells, while the target particulates M are MCF7 cells, which are human breast cancel cells. The MCF7 cells M are bondable with PE molecules so that PE molecule is selected as the bonding molecule P for labeling the particulates M with the immunomagnetic beads C.

Figure 5:
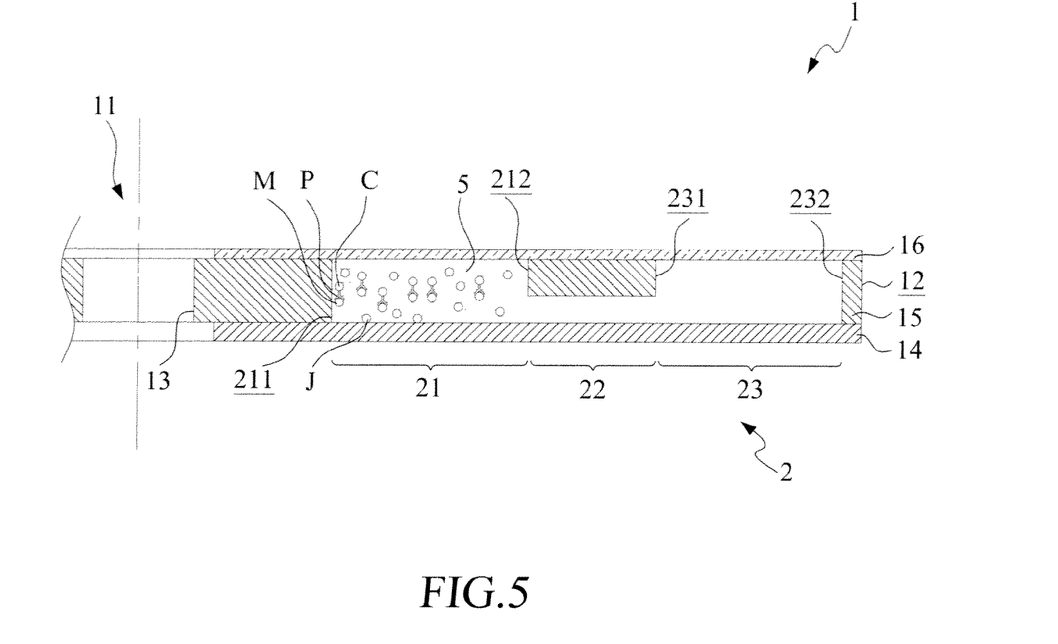
FIG. 5 is a schematic cross-sectional view illustrating a sample fluid is injected into an inner reservoir of the carrier board according to the present invention.
Figure 6:
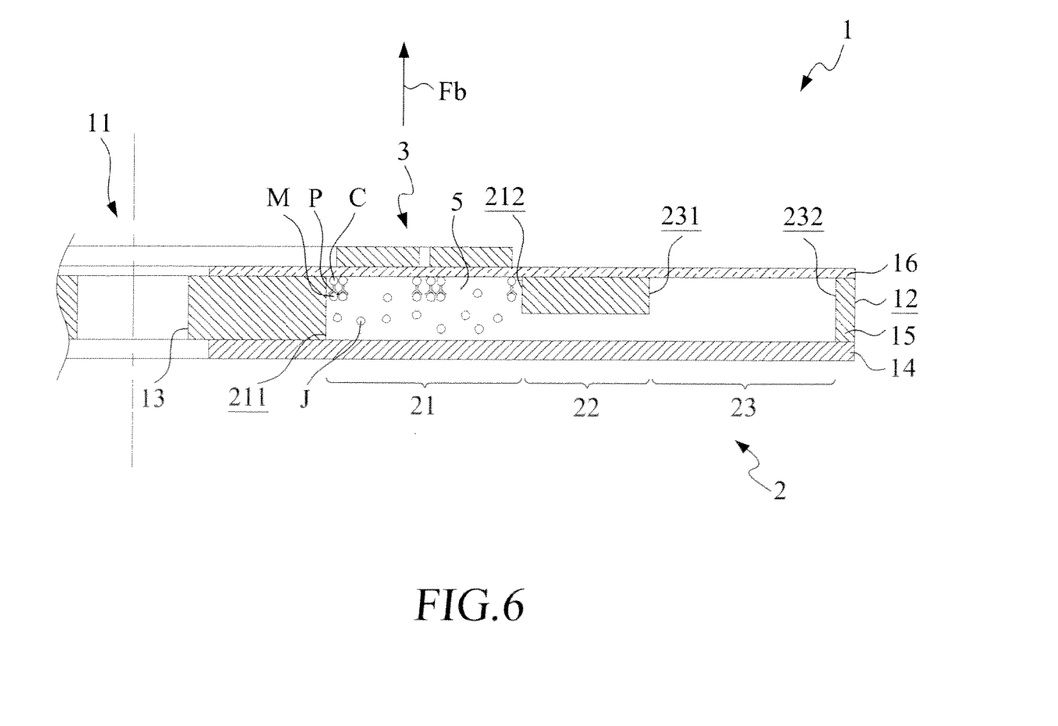
FIG. 6 is a schematic cross-sectional view illustrating a magnetic attraction force being applied according to the present invention.

As shown in FIG. 5, after the particulates M are labeled with the immunomagnetic beads C, the sample fluid 5 is injected through the fluid inlet opening 213 into the inner reservoir 21 (Step 102). Afterwards, as shown in FIG. 6, the magnetic attraction unit 3 is arranged atop the carrier board 1 and close to the inner reservoir 21 to apply a magnetic attraction force Fb that has a predetermined distribution of intensity and covers the inner reservoir 21 (Step 103).

The magnetic attraction unit 3 can be formed by arranging one or multiple magnets and in the instant embodiment, a plurality of concentrically arranged magnetic rings is adopted to generate a magnetic force Fb that has a high magnetic gradient. Generally, a magnet has a stronger magnetic force at a marginal area and a weaker one at a central area, so that the arrangement of multiple magnets is to provide as many marginal areas as possible to thereby show magnetic forces of high magnetic gradient and provide better magnetic attraction.

Afterwards, the carrier board 1 is acted upon by a driving force so that the sample fluid 5 is driven to flow through a predetermined driving strength modulation mode (Step 104). In the instant embodiment, the driving force is a centrifugal force induced by the rotation of the carrier board 1 by the driving device 4. The centrifugal force causes the sample fluid 5 to flow. In a practical application, pressure or surface tension can be adopted instead. For example, a pressure pump can be employed to apply a pressure to cause the sample fluid 5 to flow; or a surface tension caused by capillarity can be used to cause the sample fluid 5 to flow.

Figure 7:
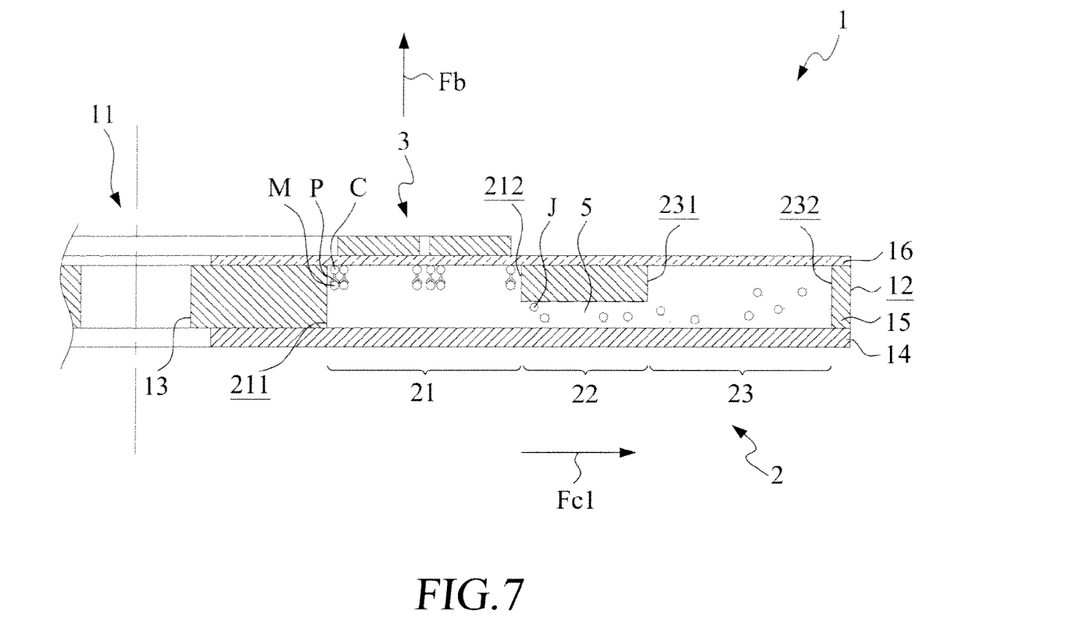
FIG. 7 is a schematic cross-sectional view illustrating a driving force having a first driving strength is being applied according to the present invention.
Figure 8:
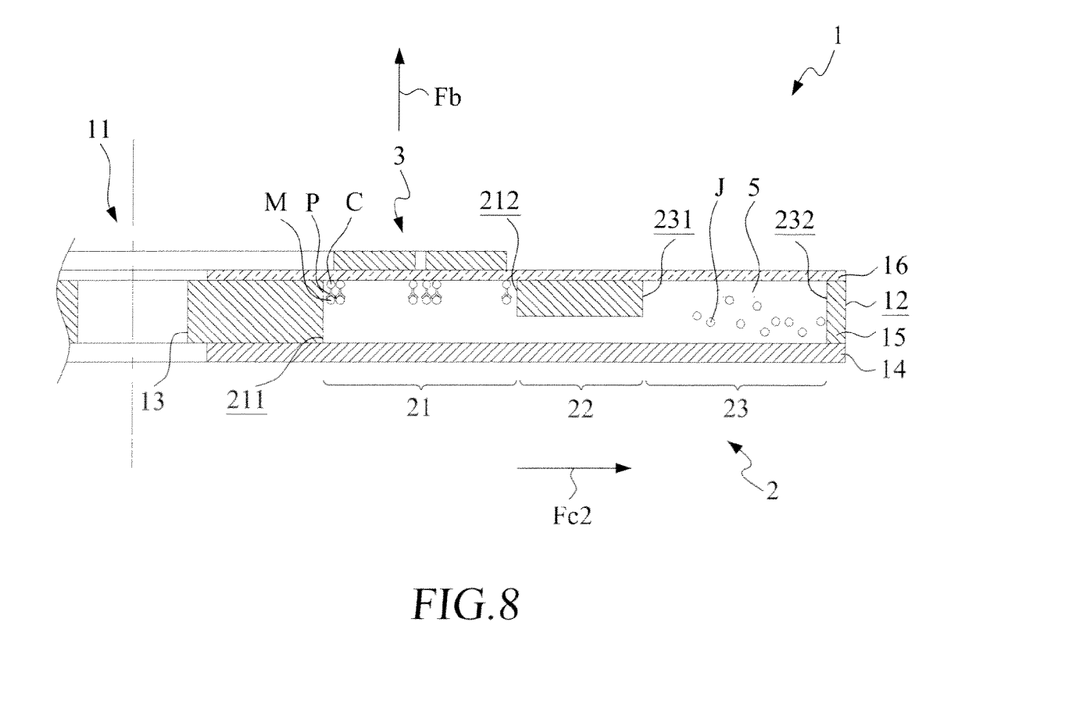
FIG. 8 is a schematic cross-sectional view illustrating a driving force having a second driving strength is being applied according to the present invention.

Referring to FIGS. 7 and 8, the driving strength modulation mode comprises first applying a driving force Fc1 that has a first, weak driving strength to drive the sample fluid 5 to flow (Step 104a) and then applying at least one driving force Fc2 that has a second driving strength exceeding the first driving strength (Step 104b). In other words, the carrier board 1 is subjected to rotation from a low rotating speed to a high rotating speed to induce the driving forces Fc1, Fc2 (which are centrifugal forces in the embodiment), so as to make the sample fluid 5 flowing.

With the driving forces Fc1, Fc2 so applied, the particulates J that are not labeled with the immunomagnetic beads C entrains the sample fluid 5 to flow through the micro flow channels 22 to be collected in the outer reservoir 23 (Step 105). Further, the magnetic force Fb applied by the magnetic attraction unit 3 retains the target particulates M that are labeled with the immunomagnetic beads C in the inner reservoir 21 (Step 106). In this way, the target particulates M are separated from the sample fluid 5.

Figure 9:
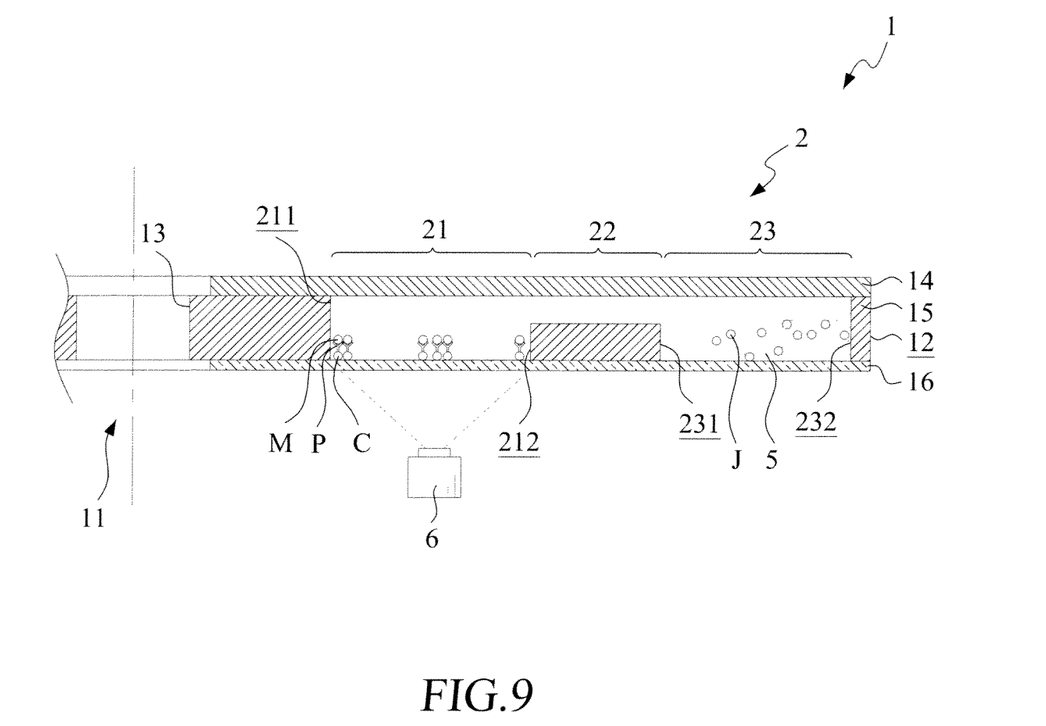
FIG. 9 is a schematic cross-sectional view illustrating observation is made on target particulates according to the present invention.

Referring to FIG. 9, after the target particulates M are separated, an observation equipment 6 (such as a microscope) is used to observe the target particulates M that are labeled with the immunomagnetic beads C retained in the inner reservoir 21 (Step 107) and other subsequent processing can be carried out. In the instant embodiment, to observe the target particulates M that are labeled with immunomagnetic beads C retained in the inner reservoir 21, the carrier board 1 is turned up side down, and the magnetic attraction unit 3 is removed to allow observation to be made through the cover layer 16 on the top side of the carrier board 1. If the carrier board 1 is not placed up side down, then upon the removal of the magnetic attraction unit 3, the target particulates M that are labeled with immunomagnetic beads C may fall down to the bottom of the carrier board 2, making it hard to observe. Further, in case it is desired to recover the target particulates M, the cover layer 16 may be formed with preset cutting lines 24 so that at least a portion of the carrier board 1 and the target particulates M that are labeled with immunomagnetic beads C can be cut off and separated from the carrier board 1 (Step 108). In this way, the target particulates M retained in the inner reservoir 21 can be efficiently recover for subsequent uses of cultivation of cells and experimentation.

Figure 10:
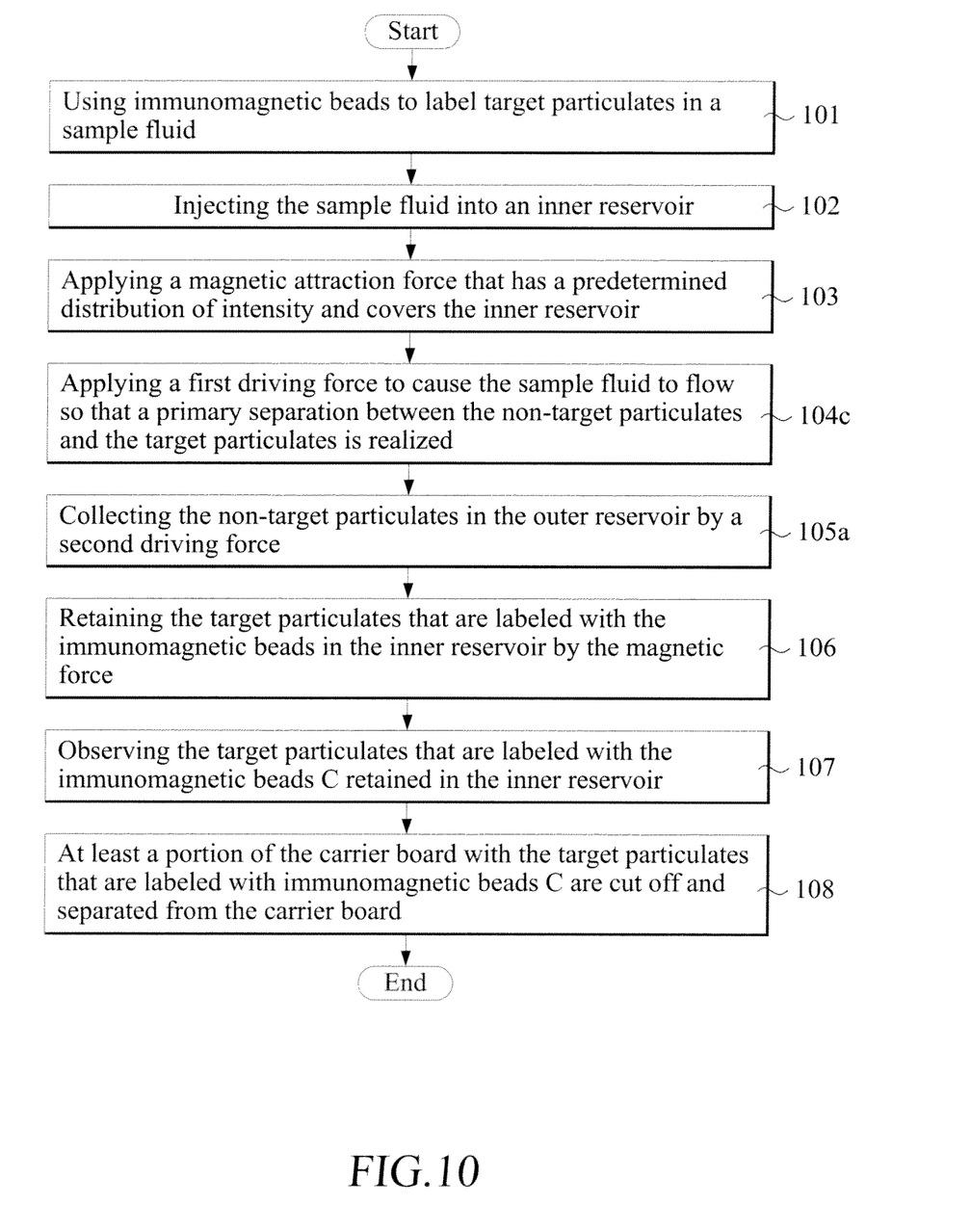
FIG. 10 is a flow chart illustrating a process in accordance with a second embodiment of the present invention.

Referring to FIG. 10, which shows a flow chart of a process in accordance with a second embodiment of the present invention, the process of the second embodiment is substantially similar to the process of the first embodiment and thus similar steps are labeled with the same reference numerals. A difference between the processes of the first and second embodiments is that in the application of the driving forces, a driving force Fc1 that has a first driving strength is first applied to cause the sample fluid 5 to flow so that a primary separation between the non-target particulates J that are not labeled with the immunomagnetic beads C and the target particulates M that are labeled with immunomagnetic beads C contained in the sample fluid 5 is realized (Step 104c). The primary separation is performed with a first, low rotating speed that rotates the carrier board 1 so that the centrifugal force Fc1 induced by the rotation of the carrier board 1 is low, thereby preventing the target particulates M from directly flowing toward the outer reservoir 23 and protecting the target particulates M from damage.

Thereafter, a driving force Fc2 of a second driving strength is applied to cause the sample fluid 5 to flow, in order to make the non-target particulates J that are not labeled with the immunomagnetic beads C entraining the sample fluid 5 to pass through the micro flow channels 22 for flowing into the outer reservoir 23 (Step 105a). Since the driving force Fc2 of the second driving strength is of a greater strength (greater centrifugal force), the amount of sample fluid 5, as well as the non-target particulates J that are not labeled with the immunomagnetic beads C, which remains in the inner reservoir 21 can be expelled to the outer reservoir 23.

Figure 11:
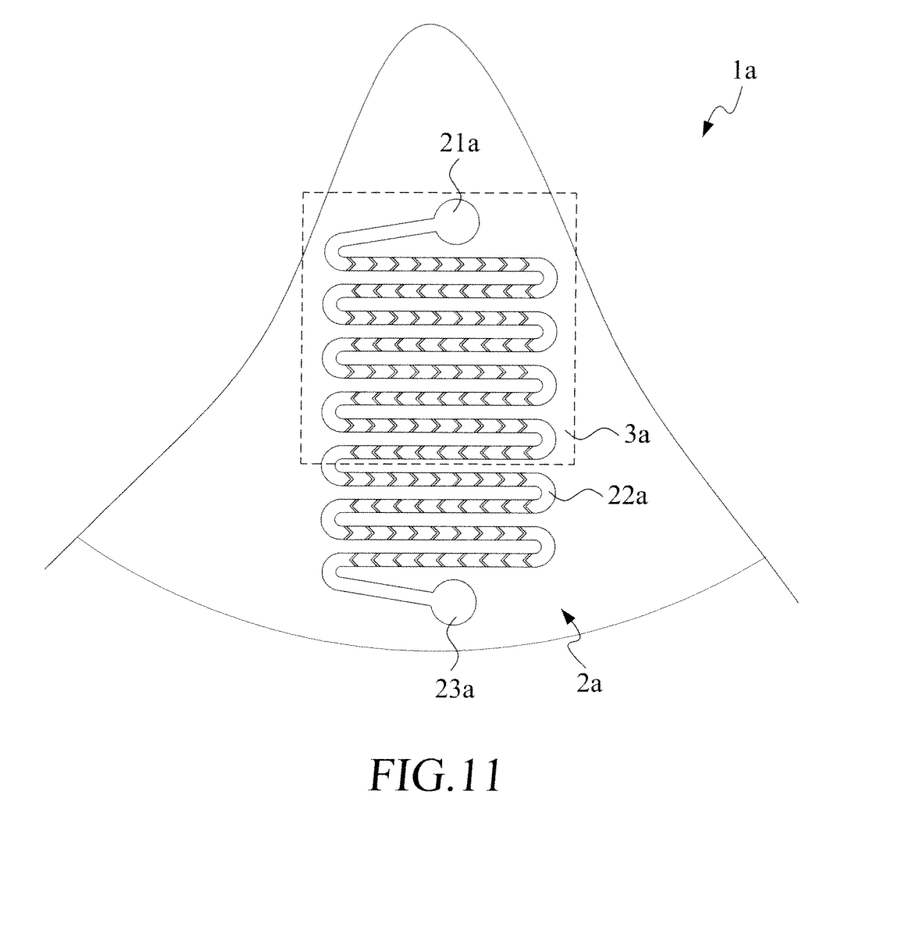
FIG. 11 is a top plan view of a portion of another carrier board in accordance with the present invention.

Referring to FIG. 11, a modified carrier board 1a with which particulate separation performed according to the present invention is carried out is shown. The carrier board 1a forms therein at least one flow channel structure 2a. Each flow channel structure 2a comprises an inner reservoir 21a, a micro flow channel 22a, and an outer reservoir 23. The micro flow channel 22a communicates between the inner reservoir 21 and the micro flow channels 22 and is of a curved structure, which exhibits an advantage of forming an extended length of flow channel in a limited space.

Figure 12:
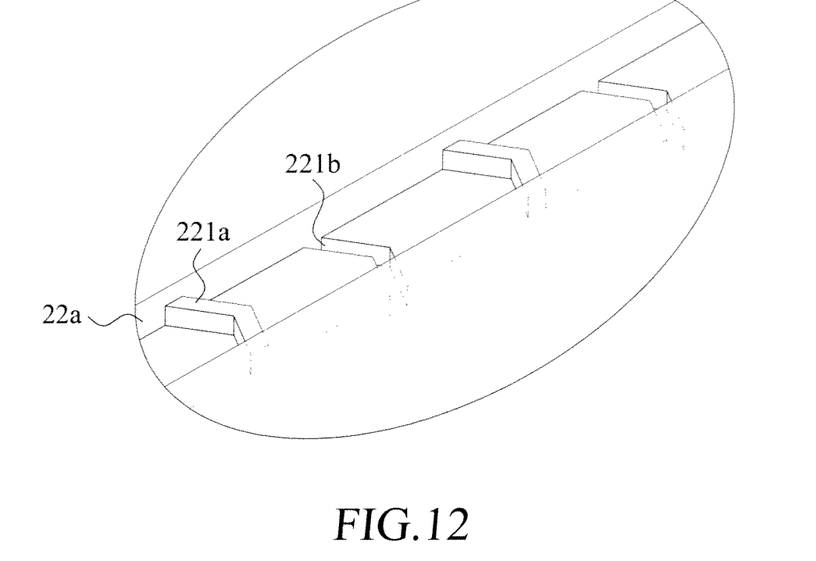
FIG. 12 is a perspective view showing another micro flow channel according to the present invention.
Figure 13:
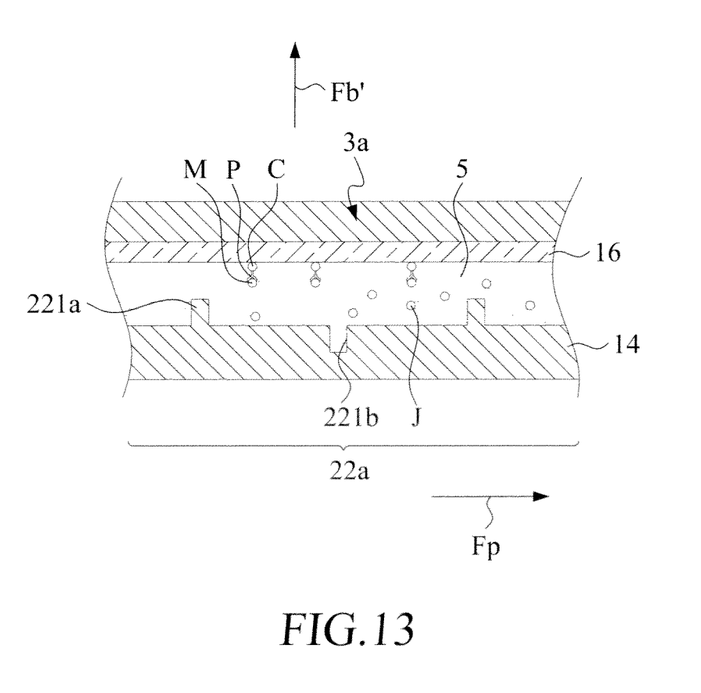
FIG. 13 is a cross-sectional view of the another micro flow channel according to the present invention.

Referring to FIGS. 12 and 13, the micro flow channel 22a forms therein a plurality of raised structures 221a and recessed structures 221b for enhancing flow turbulences, whereby when the sample fluid 5 is flowing through the micro flow channel 22a, particulates that are easily settled down to the bottom region can be easily transferred to the top region so that they can be effectively captured by magnetic attraction. Above the micro flow channel 22a, a magnetic attraction unit 3a is provided, which generates a magnetic attraction force Fb' that covers both the inner reservoir 21a and the micro flow channel 22a.

Figure 14:
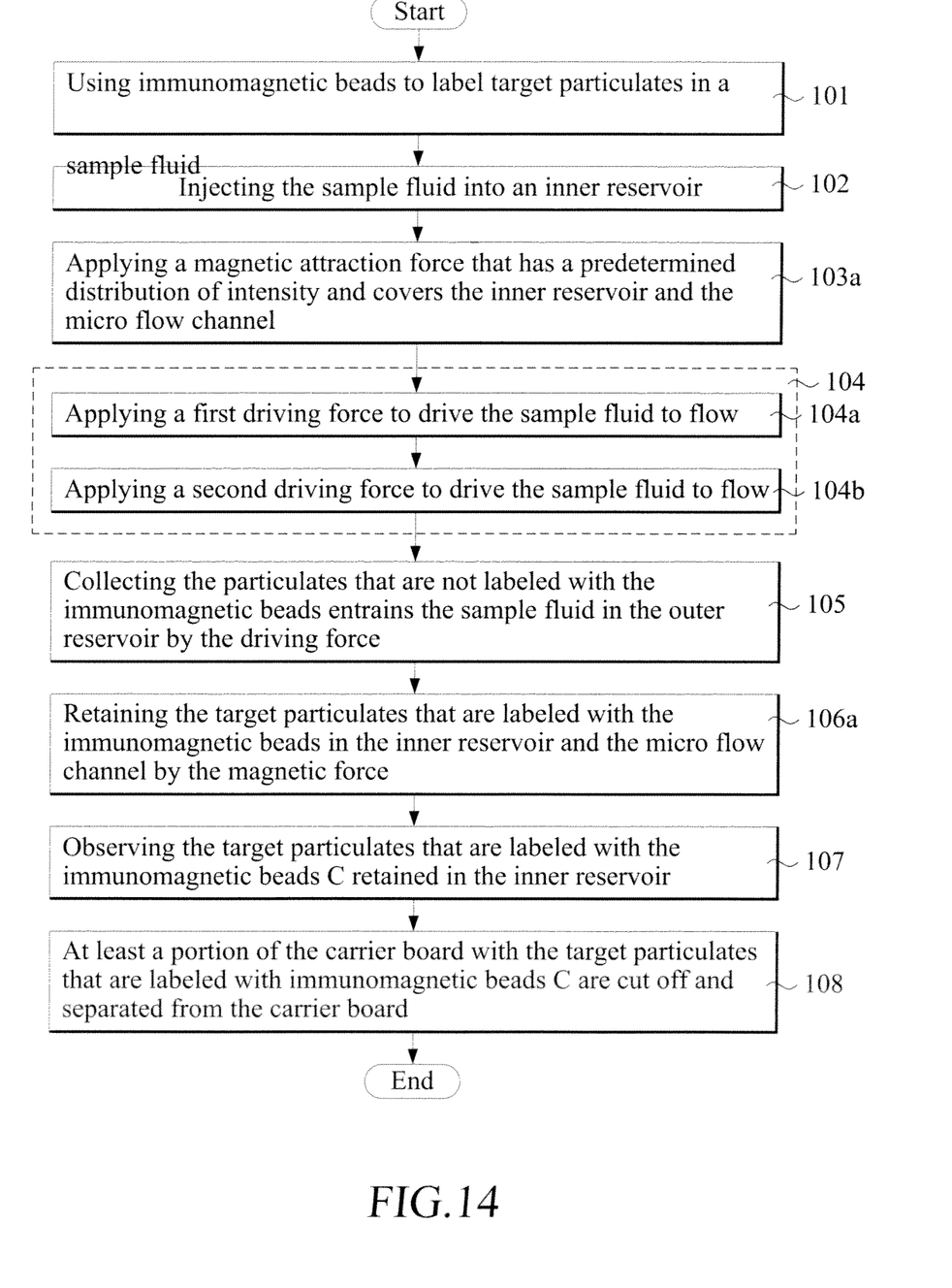
FIG. 14 is a flow chart illustrating a process in accordance with a first embodiment of the present invention.

Referring to FIG. 14, which shows a flow chart of a process according to a third embodiment of the present invention, the process will be explained as follows, with reference also had to FIGS. 11-13. The process of the third embodiment is substantially similar to the process of the first embodiment and thus similar steps are labeled with the same reference numerals. A difference between the processes of the first and third embodiments is that in the application of the magnetic attraction force, a magnetic attraction force Fb' that covers the inner reservoir 21a and the micro flow channel 22a and shows a predetermined distribution of intensity is applied (Step 103a). This, when cooperating with the raised structures 221a and the recessed structures 221b of the micro flow channel 22a, realizes an effective result of capturing. In the instant embodiment, the driving force Fp applied is pressure, wherein the pressure causes the sample fluid to flow toward the outer reservoir 23a. It is apparent that a centrifugal force or a surface tension can be used as the driving force to cause the sample fluid to flow and then the magnetic attraction force Fb' can be used to attract and retain the target particulates M that are labeled with immunomagnetic beads C in the inner reservoir 21a and the micro flow channel 22a (Step 106a).

Although the present invention has been described with reference to the preferred embodiment thereof and the best mode for carrying the invention, it is apparent to those skilled in the art that a variety of modifications and changes may be made without departing from the scope of the present invention which is intended to be defined by the appended claims.

What is claimed is:

1. A method for separating immunomagnetic bead labeled particulates with a carrier board that forms at least one flow channel structure thereon, each flow channel structure comprising an inner reservoir having at least one fluid inlet opening, an outer reservoir arranged adjacent to the inner reservoir, and at least one micro flow channel communicating between the inner reservoir and the outer reservoir, the method comprising the steps of:
    (a) in a sample fluid containing target particulates and non-target particulates, labeling the target particulates with immunomagnetic beads having a predetermined bonding molecule;
    (b) conducting the sample fluid through the fluid inlet opening into the inner reservoir;
    (c) applying a magnetic attraction force having a predetermined distribution of intensity to cover the inner reservoir and retain the target particulates at predetermined positions;
    (d) applying a driving force to drive the sample fluid to flow, wherein the driving force is applied according to a driving strength modulation mode, the driving strength modulation mode including:
        (d1) applying a driving force at a first driving strength to separate the target particulates from the sample fluid within the inner reservoir; and
        (d2) adjusting the driving force to a second driving strength exceeding the first driving strength to drive the sample fluid to flow from the inner reservoir to the outer reservoir;
    (e) allowing the non-target particulates not labeled with the immunomagnetic beads to be driven by the driving force to entrain the sample fluid through the micro flow channel for being separated and collected in the outer reservoir; and
    (f) retaining the target particulates labeled with the immunomagnetic beads within the inner reservoir at the predetermined positions with the magnetic attraction force applied.

2. The method as claimed in claim 1, wherein in step (c), the magnetic attraction force is made to further cover the micro flow channel and wherein in step (f), the target particulates that are labeled with the immunomagnetic beads are also retained by the magnetic attraction within the micro flow channel.

3. The method as claimed in claim 1, wherein in step (d), the driving force comprises one of a centrifugal force, a pressure, and a surface tension.

4. The method as claimed in claim 1, wherein after step (f), a step of observing the target particulates that are labeled with the immunomagnetic beads is performed.

5. The method as claimed in claim 4, wherein the step of observing the target particulates that are labeled with the immunomagnetic beads is performed by turning the carrier board up side down and making observation through a top side of the carrier board.

6. The method as claimed in claim 1, wherein after step (f), a step of cutting at least a portion of the carrier board and the target particulates labeled with the immunomagnetic beads off the carrier board is performed.

7. A method for separating immunomagnetic bead labeled particulates with a carrier board that forms at least one flow channel structure thereon, each flow channel structure comprising an inner reservoir having at least one fluid inlet opening, an outer reservoir arranged adjacent to the inner reservoir, and at least one micro flow channel communicating between the inner reservoir and the outer reservoir, the method comprising the following steps:
    (a) in a sample fluid containing target particulates and non-target particulates, labeling the target particulates with immunomagnetic beads having a predetermined bonding molecule;
    (b) conducting the sample fluid through the fluid inlet opening into the inner reservoir;
    (c) applying a magnetic attraction force having a predetermined distribution of intensity to cover the inner reservoir and retain the target particulates at predetermined positions;
    (d) applying a driving force of a first driving strength to drive the sample fluid to flow in order to realize primary separation between the non-target particulates not labeled with the immunomagnetic beads and the target particulates labeled with the immunomagnetic beads contained in the sample fluid;
    (e) adjusting the driving force to a second driving strength to drive the sample fluid to flow and allow the non-target particulates not labeled with the immunomagnetic beads to flow with the sample fluid through the micro flow channel for separated collection therewith in the outer reservoir;
    (f) retaining the target particulates that are labeled with the immunomagnetic beads within the inner reservoir at the predetermined positions with the magnetic attraction force applied; and
    (g) observing the target particulates labeled with the immunomagnetic beads by turning the carrier board up side down and making observation through a top side of the carrier board.

8. The method as claimed in claim 7, wherein in step (c), the magnetic attraction force is made to further cover the micro flow channel and wherein in step (f), the target particulates that are labeled with the immunomagnetic beads are also retained by the magnetic attraction within the micro flow channel.

9. The method as claimed in claim 7, wherein in steps (d) and (e), the driving force comprises one of a centrifugal force, a pressure, and a surface tension.

10. The method as claimed in claim 7, wherein after step (f), a step of cutting at least a portion of the carrier board and the target particulates labeled with the immunomagnetic beads off the carrier board is performed.

* * * * *